United States Patent
Hladio

(10) Patent No.: US 11,160,610 B2
(45) Date of Patent: Nov. 2, 2021

(54) SYSTEMS AND METHODS FOR SOFT TISSUE NAVIGATION

(71) Applicant: INTELLIJOINT SURGICAL INC., Waterloo (CA)

(72) Inventor: Andre Novomir Hladio, Hamilton (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 699 days.

(21) Appl. No.: 15/890,644

(22) Filed: Feb. 7, 2018

(65) Prior Publication Data

US 2018/0221093 A1 Aug. 9, 2018

Related U.S. Application Data

(60) Provisional application No. 62/455,851, filed on Feb. 7, 2017.

(51) Int. Cl.
*A61B 34/10* (2016.01)
*A61B 34/20* (2016.01)
(Continued)

(52) U.S. Cl.
CPC .............. *A61B 34/10* (2016.02); *A61B 5/061* (2013.01); *A61B 34/20* (2016.02); *A61B 90/39* (2016.02);
(Continued)

(58) Field of Classification Search
None
See application file for complete search history.

(56) References Cited

U.S. PATENT DOCUMENTS 5,768,156 A * 6/1998 Tautges ................... G06T 17/20
703/2
2005/0101855 A1 5/2005 Miga et al.
(Continued)

FOREIGN PATENT DOCUMENTS

WO 2018047096 A1 3/2018

OTHER PUBLICATIONS

Li et al., "A framework for correcting brain retraction based on an eXtended Finite Element Method using a laser range scanner" Int. J. CARS (2014) 9:669-681. (Year: 2014).*

(Continued)

*Primary Examiner* — Yi-Shan Yang

(57) ABSTRACT

There are provided systems and methods for soft tissue navigation. A sensor unit provides tracking information to determine positional data for a patient's structural anatomy and gravity direction measurements to determine a direction of gravity relative to the anatomy. A computing unit, during a procedure, computes the direction of gravity and determines spatial information for soft tissues of the patient, responsive to the direction of gravity. Expected soft tissue movement may be provided by a computer model modelling the mechanics of the soft tissues responsive to the direction of gravity, or by other means such as look up table. Surgical navigation data is presented via a display unit. Medical images may be registered and navigation provided relative to the images. Tool positions may be tracked via the sensor unit. Spatial differences in soft tissues between orientations of the patient (relative to gravity) may be determined and presented.

23 Claims, 7 Drawing Sheets

(51) Int. Cl.
*A61B 90/00* (2016.01)
*A61B 5/06* (2006.01)
*A61B 5/03* (2006.01)
*A61B 5/021* (2006.01)

(52) U.S. Cl.
CPC ............... *A61B 5/021* (2013.01); *A61B 5/031* (2013.01); *A61B 5/066* (2013.01); *A61B 5/067* (2013.01); *A61B 2034/104* (2016.02); *A61B 2034/105* (2016.02); *A61B 2034/2048* (2016.02); *A61B 2034/2055* (2016.02); *A61B 2034/2065* (2016.02); *A61B 2090/3908* (2016.02); *A61B 2090/3983* (2016.02)

(56) References Cited

U.S. PATENT DOCUMENTS

| | | | | |
|---|---|---|---|---|
| 2007/0253541 | A1* | 11/2007 | Sukovic | A61B 34/20 378/205 |
| 2011/0196377 | A1* | 8/2011 | Hodorek | A61B 17/157 606/87 |
| 2014/0049629 | A1* | 2/2014 | Siewerdsen | A61B 34/20 348/77 |
| 2016/0249987 | A1* | 9/2016 | Hladio | A61B 90/06 606/102 |
| 2017/0143433 | A1 | 5/2017 | Fanson et al. | |
| 2017/0143494 | A1* | 5/2017 | Mahfouz | A61B 90/06 |
| 2017/0178375 | A1* | 6/2017 | Benishti | G02B 27/0172 |
| 2019/0231433 | A1* | 8/2019 | Amanatullah | A61B 17/1703 |

OTHER PUBLICATIONS

Ohue et al., "Evaluation of intraoperative brain shift using an ultrasound-linked navigation system for brain tumor surgery". Neurol. Med. Chir. 50, 291-300, 2010. (Year: 2010).*

Borgert et al., "Respiratory motion compensation with tracked internal and external sensors during CT-guided procedures". Comput. Aided Surg. May 2006; 11(3): 119-125. (Year: 2006).*

Gao et al., "Constitutive modeling of liver tissue: experiment and theory". Ann Biomed Eng. 2010; 38(2):505. (Year: 2010).*

* cited by examiner

SYSTEMS AND METHODS FOR SOFT TISSUE NAVIGATION

CROSS-REFERENCE

This application claims the benefit of U.S. Provisional Application No. 62/455,851 filed Feb. 7, 2017, which is incorporated herein by reference.

FIELD

The following disclosure relates to computer assisted procedures such as computer assisted surgical navigation and localization. More particularly, the disclosure relates to computer systems and methods for navigation of soft tissues.

BACKGROUND

Surgical navigation has commonly been used to perform accurate, minimally invasive procedures involving soft tissues. Typically, these are image-guided procedures (i.e. they are with reference to a medical image, such as an MRI scan). Example surgeries include taking biopsies, excising tumours, placing implants, etc. A challenge with surgical navigation of soft tissues stems from the fact that soft tissues are deformable, and therefore may move based on any applied forces. One such force is gravity.

Additional background for the use of navigation systems in cranial surgery is discussed in "Evaluation of intraoperative brain shift using an ultrasound-linked navigation system for brain tumor surgery", S. Ohue et al, Neurol Med Chir (Tokyo) 50, 291~300, 2010, the entire content of which is incorporated herein by reference.

SUMMARY

There are provided systems and methods for soft tissue navigation. A sensor unit provides tracking information to determine positional data for a patient's structural anatomy and gravity direction measurements to determine a direction of gravity relative to the anatomy. A computing unit, during a procedure, computes the direction of gravity and determines spatial information for soft tissues of the patient, responsive to the direction of gravity. Expected soft tissue movement may be provided by a computer model modelling the mechanics of the soft tissues responsive to the direction of gravity, or by other means such as look up table. Surgical navigation data is presented via a display unit. Medical images may be registered and navigation provided relative to the images. Tool positions may be tracked via the sensor unit. Spatial differences in soft tissues between orientations of the patient (relative to gravity) may be determined and presented.

In an example, there is provided a system to perform a surgical procedure on soft tissues. The system comprises a sensor unit, comprising an optical sensor to generate optical measurements from a tracker and at least one other sensor to provide inclination measurements to determine a direction of gravity, wherein the tracker is configured to provide positional information in up to six degrees of freedom to the optical sensor; a reference element to couple with a structural member of a patient's anatomy; and a computing unit. The computing unit is configured to: compute a registration of the structural member of the patient's anatomy relative to the reference element; calculate a direction of gravity relative to the structural member of the patient's anatomy based on the inclination measurements and the registration; determine spatial information of the soft tissues relative to the reference element based on the registration, the direction of gravity, and expected soft tissue movement provided by a computer model modelling the mechanics of the soft tissues of the patient's anatomy responsive to the direction of gravity; and provide surgical navigation data for display.

In an example there is provided a system to perform a surgical procedure on soft tissues. The system comprises a sensor unit, comprising an optical sensor to generate optical measurements from a tracker and at least one sensor to provide inclination measurements to determine a direction of gravity, wherein the tracker is configured to provide positional information in up to six degrees of freedom to the optical sensor; a reference element to couple with a structural member of a patient's anatomy; and a computing unit. The computing unit is configured to: receive medical image data of the patient's anatomy including the soft tissues, the patient's anatomy being in a first known orientation with respect to gravity during imaging; compute a registration of the structural member of the patient's anatomy relative to the reference element; calculate a second orientation with respect to gravity of a patient's anatomy based on inclination measurements and the registration; calculate the orientation difference between the first known orientation and the second orientation; and provide the orientation difference for display.

In an example, there is provided a system to perform a surgical procedure on soft tissues of a patient's anatomy. The system comprises a sensor unit, comprising an optical sensor to generate optical measurements from a tracker and at least one sensor to provide inclination measurements to determine a direction of gravity, wherein the tracker is configured to provide positional information in up to six degrees of freedom to the optical sensor; a reference element to couple with a structural member of the patient's anatomy; and a computing unit. The computing unit is configured to: compute a registration of the structural member of the patient's anatomy relative to the reference element; calculate a direction of gravity relative to the structural member of the patient's anatomy based on inclination measurements and the registration; provide the direction of gravity to a computer model modelling the mechanics of the soft tissues of the anatomy; and receive data from the computer model regarding a shift of the soft tissues of the anatomy. The surgical procedure may be a cranial procedure and the shift may be a shift of a brain.

When a computing unit is described as being "configured to" perform certain operations, it may be configured via instructions stored in a storage device which when executed by one or more processing units configure the operations of the computing unit or it may be hardware configured such as by an application specific circuit (ASIC) or other circuits.

DESCRIPTION

Reference in the specification to "one embodiment", "preferred embodiment", "an embodiment", or "embodiments" means that a particular feature, structure, characteristic, or function described in connection with the embodiment is included in at least one embodiment, and may be in more than one embodiment. Also, such phrases in various places in the specification are not necessarily all referring to the same embodiment or embodiments.

Surgical navigation of soft tissues is provided, including compensation for the effect of gravity on the position of the soft tissues. Cranial navigation will be used as the primary exemplary application, although it will be appreciated by those skilled in the art that the described systems and methods may be applied to other types of surgery involving soft tissues.

Figure 1:
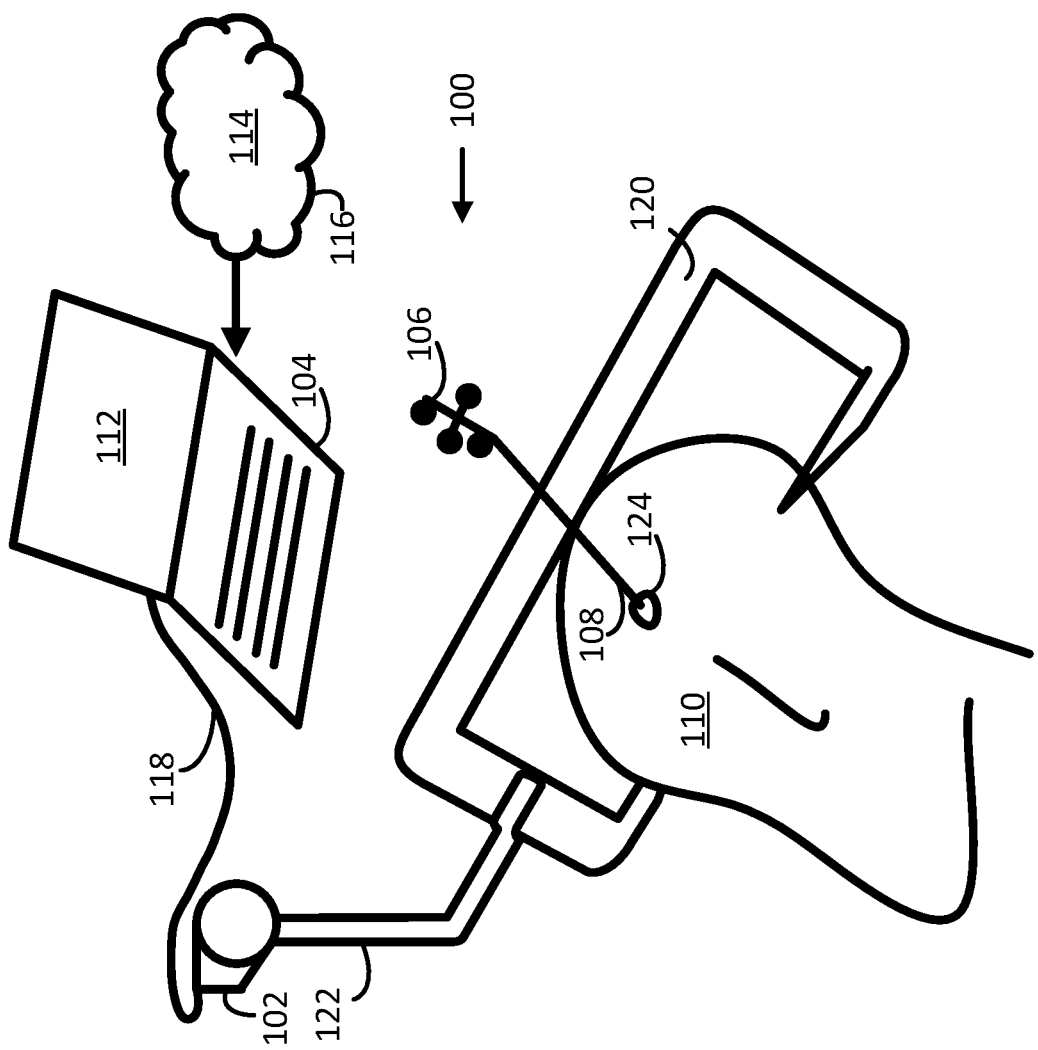
FIG. 1 is a representation of an intra-operative localization system in accordance with one example configuration where an optical sensor is mounted to a head clamp.
Figure 2:
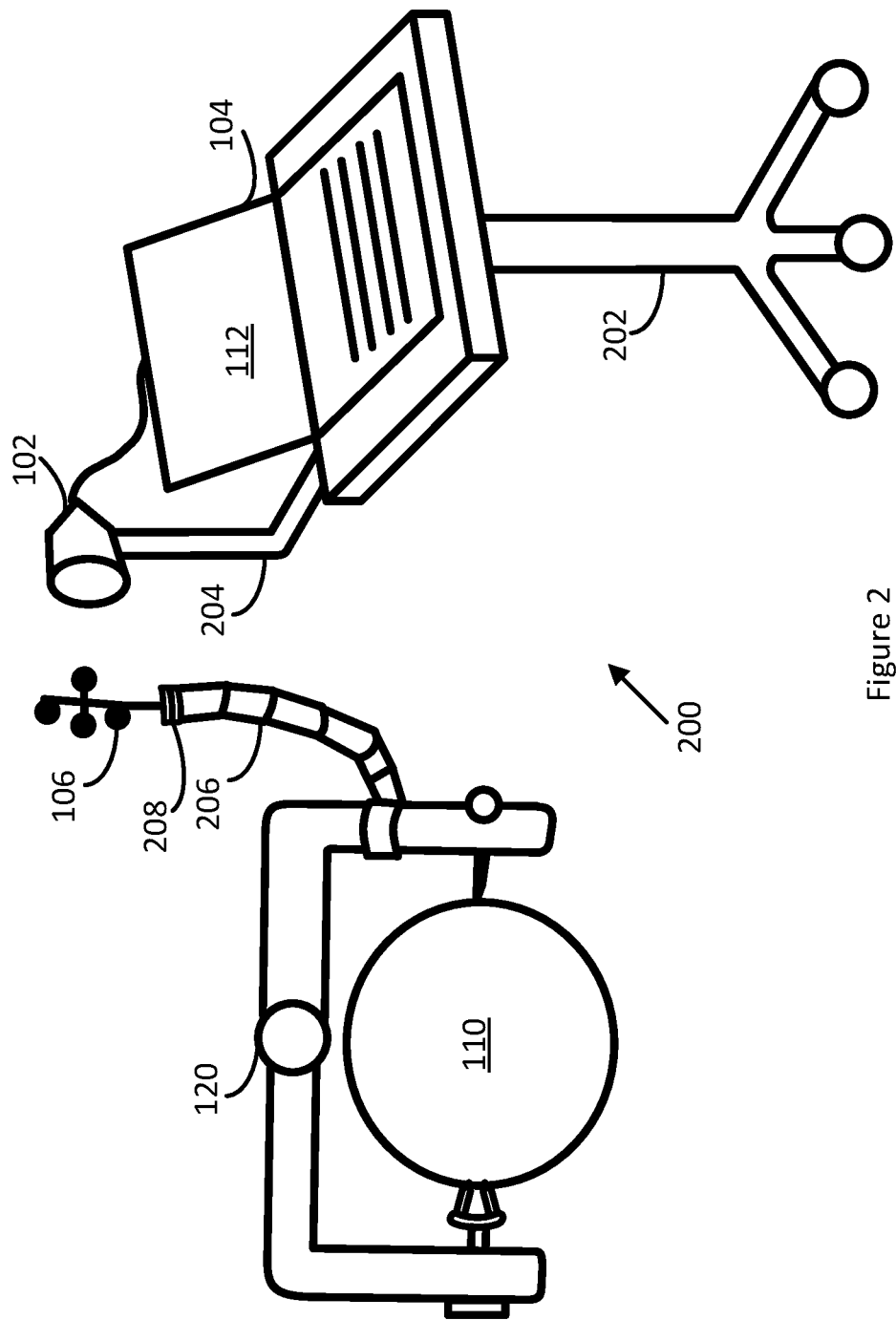
FIG. 2 is a representation of an intra-operative localization system in accordance with one example configuration where an optical sensor is mounted to an OR cart supporting an intra-operative computing unit.
Figure 3:
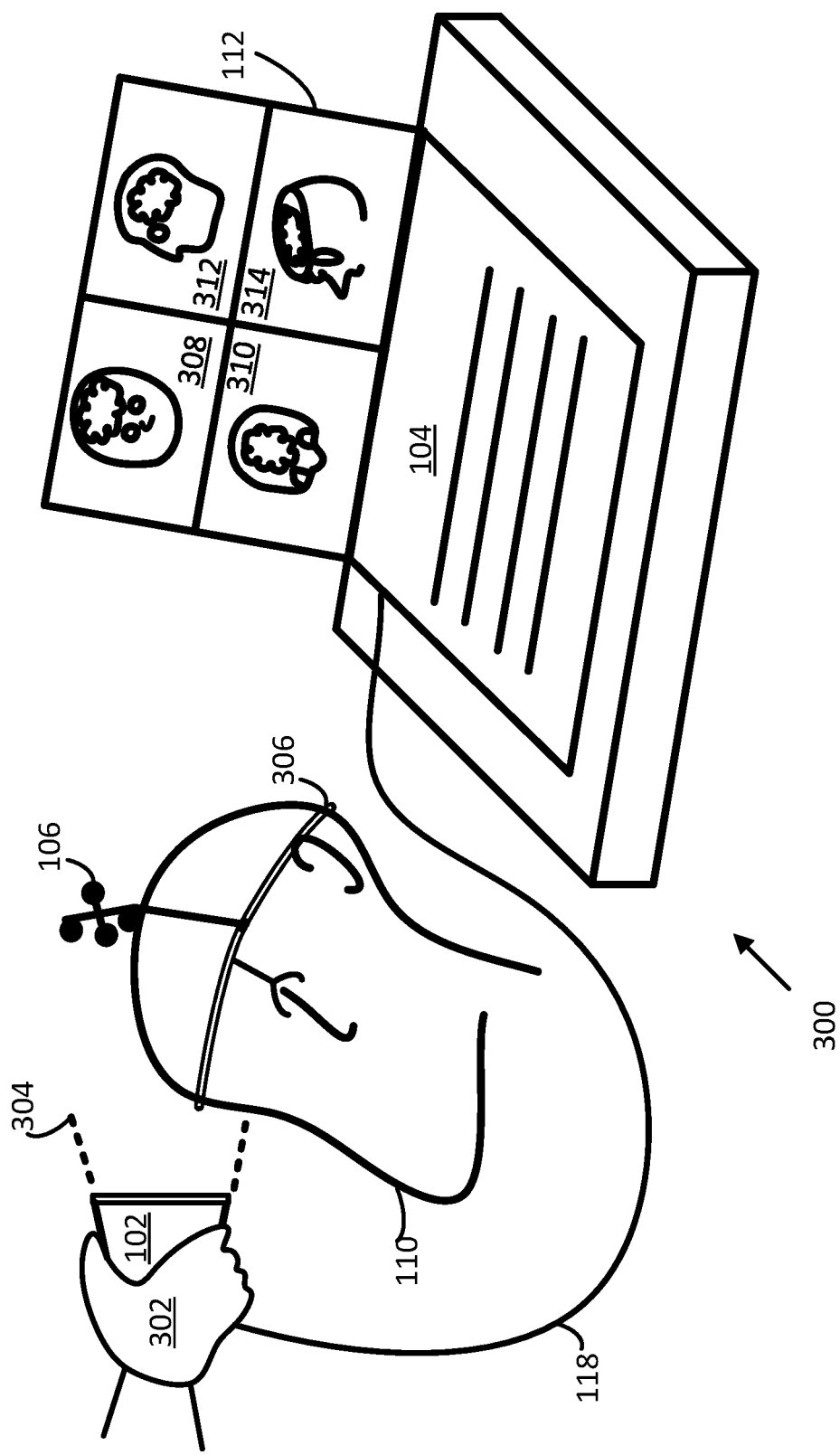
FIG. 3 is a representation of an intra-operative localization system in accordance with one example configuration where an optical sensor is hand held. Further a display unit shows a representative graphical user interface providing a 4-Up view of medical images of a patient's skull.

A cranial navigation system is described in U.S. provisional application No. 62/384,410, filed Sep. 7, 2016 of Hladio et al., and entitled "Systems and Methods for Surgical Navigation, Including Image-Guided Navigation of a Patient's Head", formalized as PCT/IB2017/055400 filed Sep. 7, 2017, the entire contents of which are incorporated herein by reference. A reference element is attached to the patient's skull (via a head clamp). The skull provides a structural member of the patient's anatomy that is rigid. A "structural member" as used herein is a part of the patient's anatomy that provides a stable surface (e.g. a bone) that is not prone to or is less susceptible to deformation due to factors such as gravity, pressure, etc. The structural member may also allow the reference element to be attached to it. The brain is a soft tissue organ; it has a nominal spatial location within the skull, but is free to move (i.e. shift, deform) to an extent. When attempting to localize a small region (e.g. a region of interest) in the brain, the movement may be significant, and should be accounted for. An exemplary intra-operative localization system 100 is shown in FIG. 1 in accordance with an example. Additional examples of intra-operative localization systems (200 and 300) are shown in FIGS. 2 and 3 respectively.

In FIG. 1, an optical sensor 102 (depicted as a camera) is connected to a workstation 104 (i.e. a computing unit) to provide optical signals for generating positional measurements of a tracker 106 visible to the sensor. The tracker is configured to provide positional information in up to six degrees of freedom to the optical sensor 102. The workstation 104 executes instructions to provide surgical navigation of a surgical tool 108 (depicted as a probe coupled to tracker 106) with respect to the brain of a patient 110. The workstation 104 may comprise or be coupled to a display unit 112 for displaying user interfaces (e.g. screens) which may present measurements, medical images, live video images, workflow, etc. with respect to the procedure.

Pre-operative data 114 may be loaded onto the workstation 104. Pre-operative data may include medical images (e.g. brain or other patient images) obtained per-operatively from scans of the patient's anatomy using one or more modalities (e.g. magnetic resonance imaging (MRI)) for display. Pre-operative data may include geometric definitions of surgical tools or other objects to be tracked. During localization, workstation 104 receives sensor data from sensor 102 and determines a pose of the tracker 106. In some examples, a single tracker may be removable and coupled to different objects having different geometries. In some examples, a tracker is permanently coupled to a particular object. Workstation 104 may use the geometrical definition of the object along with the pose of the tracker to determine positional information from the object such as the pose (location) of a tip of the tool. Pre-operative data 114 may be remotely stored relative to the workstation 104 such as on a server (represented by cloud 116), on a USB device (not shown) or other storage device (not shown). Pre-operative data 114 may be stored on a hard drive or other storage device (both not shown) of workstation 104. Workstation 104 may have a communication system (not shown) for communicating data wirelessly or in a wired manner. The communication system may have one or more interfaces (not shown), for example, to couple the workstation to sensor 102 such as via a cable 118. Workstation 104 may comprise one or more processing units for performing operations such as may be instructed by software (instructions) stored on a storage device (e.g. memory) coupled to the one or more processing units.

Sensor 102 is coupled to the anatomy of the patient 110 (the patient's skull) using a head clamp 120 and sensor arm 122 to rigidly couple the sensor to a rigid structure of the patient. A craniotomy 124 receives a tip of surgical tool 108. Workstation 104 may track the location of the tip of the tool via tracker 106 even though the tip may not be visible when located within the skull (and brain tissue).

FIG. 2 shows an example of a localization system 200 in which the sensor 102 is coupled to an OR cart 202 via a sensor arm 204. In this configuration, the (optical) tracker 106 is coupled to the patient 110 via head clamp 120 and a tracker arm 206. The tracker may be removably coupled to the tracker arm 206 via a kinematic (e.g. magnetic) mount 208 to position the tracker in a same position each time it is coupled to the tracker arm 206. A separate optical tracker (not shown) or optical tracker 106 may be coupled to a surgical tool (not shown in FIG. 2), which tool may be tracked during a procedure. Provided that the camera and patient remain stationary following a registration procedure (as described below), tracker 106 may be removed from tracker arm 206 and used on a tool, if desired. FIG. 2 illustrates a head clamp 120 having a different configuration than is shown in FIG. 1, which is not material to the disclosure.

FIG. 3 shows an example of a localization system 300 in which sensor 102 may be held in a hand 302 of a user such as a surgeon or other person attending in the OR. The field of view 304 may be directed at the patient 110 to capture optical measurements of tracker 106. Tracker 106 is coupled to the patient's anatomy (e.g. skull) via a tracker mounting structure 306. A display unit 112 of workstation 104 displays a user interface (UI) showing medical images (e.g. 308, 310, 312 and 314) in a 4-Up view as described further below.

Figure 6:
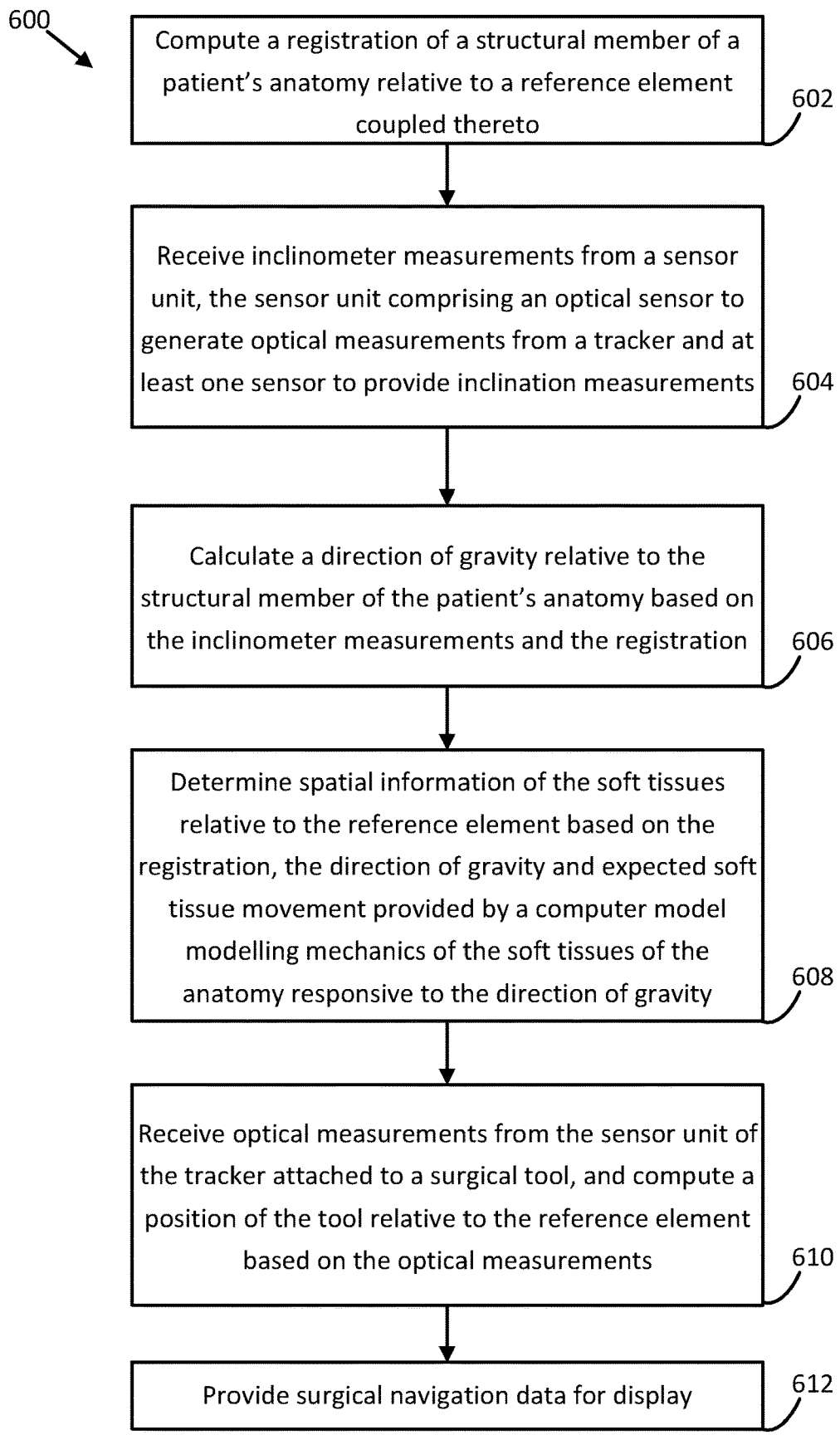
FIGS. 6 to 8 are flowcharts of respective operations of a computing unit in accordance with examples herein.

Registering the patient's anatomy to the localization system 100 is a step involving generating a mathematical spatial relationship (registration data) representing the relative position of a reference element and the patient's anatomy. The reference element may be a sensor (e.g. the sensor 102 (camera) of FIG. 1), or a tracker 106 (as illustrated in FIGS. 3 and 6). The sensor 102 is used to generate optical measurements of a tracker attached to the surgical tool 108 relative to the reference element that is coupled to a structural element of a patient's anatomy. For navigation, one tracker is attached to a surgical tool 108 (such as the probe of FIG. 1).

The registration step involves receiving inputs (e.g. a user localizing anatomical landmarks or imaging fiducials using a probe for measuring by the camera) and performing computations based on the inputs to generate registration data. In some instances, image registration is performed. Image registration entails determining the spatial relationship between the reference element and the image of the patient's anatomy, and is based on computations correlating inputs received (e.g. user inputs) with image features. Details of such image registration are included in U.S. provisional 62/384,410. Various registration tools (e.g. an axis frame, a probe with a tip, a plane registration device) may be used to perform the registration. Details of such registration tools are provided in U.S. application Ser. No. 15/425,690, filed Feb. 6, 2017 by Fanson et al. titled "Systems, methods and devices for image registration and surgical localization", published May 25, 2017 as US-2017-0143433-A1 and issued as U.S. Pat. No. 9,713,506 on Jul. 25, 2017, which are incorporated herein by reference.

Upon registration and image registration, image guided surgery may be performed. During such surgery, the position of a surgical tool (e.g. 108) relative to a patient's anatomy (e.g. a brain) is depicted relative to a medical image (e.g. an MRI) of the patient's anatomy. An exemplary view provided for display to display unit 112, from a computing unit 104, is shown in FIG. 3, in which four views of the medical image are provided. These 4-Up views may include a coronal 308, a transverse 310, a sagittal 312 and an isometric view 314.

In many types of cranial surgery, a head of a patient 110 is immobilized within a head clamp 120, the head being oriented in accordance with a surgical plan, the plan indicating a desired location for accessing the surgical site (e.g. the location of a craniotomy 124). The orientation of the head (based on the surgical plan) determines the direction of gravity during the surgical procedure. Gravity will act on the patient's tissues, including the soft tissues of interest (i.e. the brain). When oriented for surgery, the head may have an approximately known orientation with respect to gravity. Furthermore, during the surgical procedure, the head's orientation may change intentionally (e.g. due to repositioning), or unintentionally (due to movement of the head clamp 120), causing a change in the direction of gravity with respect to the brain.

Figure 4A:
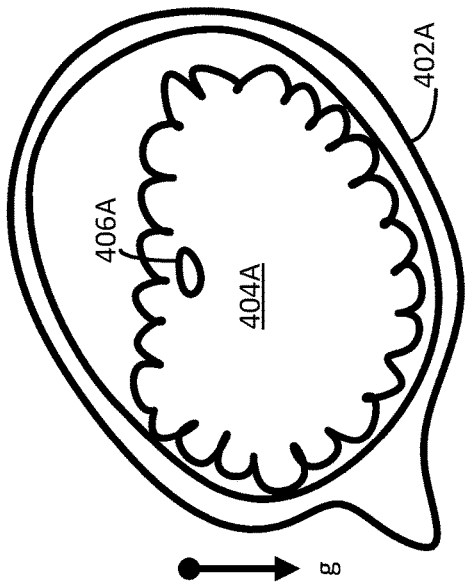
FIGS. 4A and 4B are representations of a patient skull in two orientations.
Figure 4B:
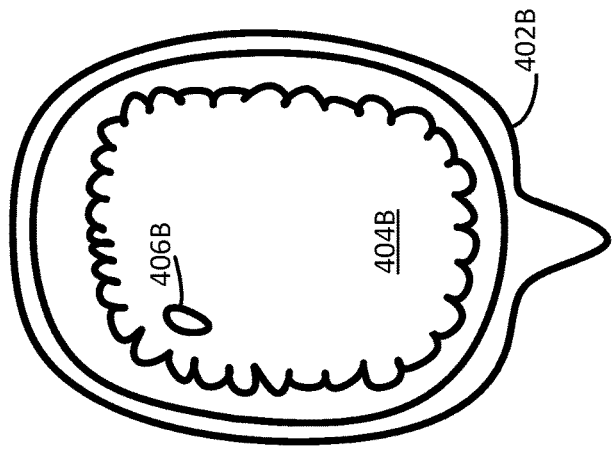

In FIGS. 4A and 4B, two respective orientations of a patient's head are depicted. In each orientation, the same anatomical tissue is depicted: a skull 402A and 402B (exemplary of a structural anatomical member), a brain 404A and 404B (exemplary of soft tissues), and a lesion 406A and 406B (exemplary of a region of interest in the soft tissues). In each orientation, the soft tissues (including the region of interest) have a different position, based at least in part on the effect of gravity (depicted as force g).

Figure 5:
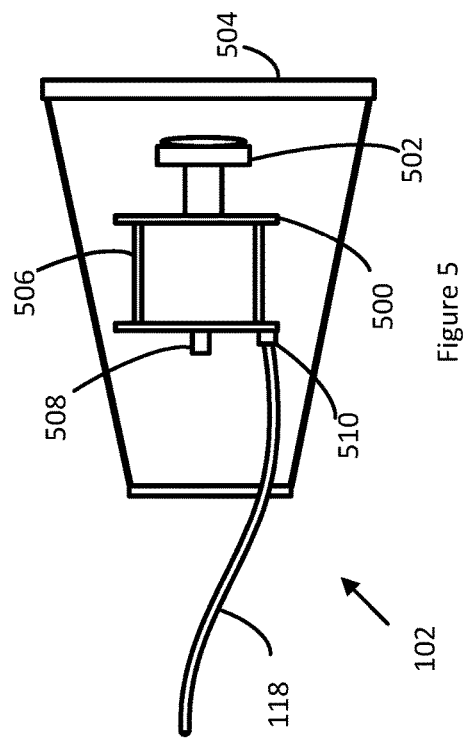
FIG. 5 is a representation of an optical sensor of a localization system, showing selected components internal to the optical sensor, in accordance with one example configuration.

As depicted in FIG. 5, sensor 102 has inclination sensing capabilities via an inclinometer (or accelerometer) integrated into the sensor 102. The sensor 102 comprises an optical sensor (a camera 500 comprising a lens 502, an optical window 504, etc.) that is connected by a rigid structure 506 to an inclinometer 508. The sensor 102 is also connected via a connector 510 to cable 118 to couple the sensor 102 to the workstation 104 (e.g. as in FIGS. 1, 3 and 6). In this case, the sensor 102 provides optical and inclination measurements, both related to a common frame of reference. Further discussion on how to enable this is provided below.

In order to provide inclination measurements, an inclinometer 508, such as an accelerometer, may be integrated within the sensor, as shown in FIG. 5. The inclinometer measurements are combined with optical measurements using techniques known in the art of sensor fusion, such that measurements are provided with a common frame of reference. A rigid structure 506 exists between the location of the camera 500 and the inclinometer 508, thus creating a rigid mechanical relationship. This relationship is unique for each physical device and is used by the workstation 104 when both the inclinometer 508 and camera 500 communicate measurements to it by any means, e.g. wired through cable 118, wireless, etc. The workstation 104 may use this relationship to align inclinometer coordinate values to the optical coordinate values, and display further calculations in the same frame of reference.

In addition to or alternative to accelerometers, other sensing components may be integrated to assist in registration and/or pose estimation. Such sensing components include, but are not limited to, gyroscopes, magnetometers, etc. It may be preferable for the sensing components to be in the form of electronic integrated circuits.

The sensor 102 provides measurements of the direction of gravity to the workstation 104. The workstation 104 is able to calculate the direction of gravity relative to the reference element. In one example (e.g. FIG. 1), the sensor 102 is the reference element, and the direction of gravity is with respect to the sensor 102 by default. In another example (e.g. FIGS. 2 and 3), a tracker 106 is the reference element; in this case, the computing unit calculates the direction of gravity relative to the sensor 102, and calculates the pose of the reference element. The direction of gravity relative to the reference element is calculated by expressing the gravity vector in the frame of reference of the reference element (i.e. using spatial mathematics).

The reference element may be coupled to a structural member of the patient's anatomy, such that any movement of the structural member of the patient's anatomy is reflected by substantially the same movement of the reference element. The reference element may be rigidly attached to the structural member of the patient's anatomy; where the structural member is bone, the reference element may be attached via one or more bone pins or screws.

The reference element may also be non-invasively attached over a patient's skin, using, for example, adhesives, suction cups, stickers, clamps, elastic bands or other mounting structures. FIG. 3 illustrates a non-invasive reference element (tracker 106) mounted via a tracker mounting structure 306, secured to the skull of the patient 110 by mating with their facial features using a glasses-like structure.

Multiple reference elements may be attached to the same structural element (not shown). One advantage of using multiple reference elements, is that there is a degree of redundancy, so that if one reference element's position with respect to the structural member changes, this would be detectable and/or correctable by detection and/or correction functions executing on the computing unit (i.e. where the other reference element does not move).

Registration of a structural member of the patient's anatomy may be performed, since it may be difficult and impractical to register the soft tissues of interest, due to soft tissue movement and difficulty attaching a reference element directly to soft tissues. For example, a patient's skull may be registered, since it is impractical to directly register a patient's brain due to the fact that the procedure may be minimally invasive, and only a small part of the brain is exposed. Also, it is not practical to attach a reference element to the brain, whereas attaching a reference element to the skull (via head clamp 120, as shown in FIG. 2 or tracker mounting structure 306 of FIG. 3) is feasible. Furthermore, the brain is expected to move during the procedure.

The soft tissues may have a nominal position relative to the structural member of the patient's anatomy. The position of the soft tissues with respect to the structural member of the patient's anatomy is based on mechanics. Various mechanical factors may influence this relative position, including: the direction of gravity; pressure (e.g. if the soft tissues are within a structural cavity, the pressure within the cavity); blood pressure; tissue material properties, including properties of aged or diseased tissues; and, the size and shape of tissues.

A computer model of the mechanics of soft tissues is implemented as a software module as described in U.S. publication no. 20050101855 A1 published 12 May 2005 of Miga et al., titled "Apparatus And Methods Of Brain Shift Compensation And Applications Of The Same", the contents of which are incorporated by reference herein. The software module receives inputs, at least including the direction of gravity relative to the structural member of the patient's anatomy, and performs computations to generate outputs, including the expected soft tissue position relative to the structural anatomical member. Inputs to the software module may include any parameter that helps predict the position of the soft tissues with respect to the structural member of the patient's anatomy. The expected position of the soft tissues is governed by the mechanics of the patient's anatomy, including environmental factors (e.g. the direction of gravity).

The mechanics include forces, displacements, pressures, etc. within the patient's anatomy. The computer model of the mechanics of the soft tissue may be implemented in software, for example, as a finite element model, a look-up table, an anatomical atlas, a differential equation solver, a machine learning algorithm, etc. Any software implementation that predicts, with sufficient accuracy for the surgical procedure, the position of the soft tissues may be used.

The inputs may include a medical image of the patient's anatomy, including the structural member and the soft tissues of interest. Another input may include the direction of gravity during image acquisition relative to the medical image, expressed as a vector in the image coordinate system. The medical image may be a raw medical image (such as an MRI or computed tomography (CT) scan) or a fused image combining multiple modalities. Image segmentation may be used to differentiate the various tissues within the medical image—for example, the structural anatomical members, the soft tissues, including regions of interest within the soft tissues (e.g. a region of interest may be a tumour or lesion within the brain, within the skull). Image segmentation may be performed by a separate computing unit, and a segmented image may be provided to the software module as an input. Alternatively, the software module may perform image segmentation, where an unsegmented image is provided as an input.

Pressure (e.g. within a cavity containing the soft tissues) may be provided as an input. For example, during a cranial procedure, the pressure within the skull may change as a result of a craniotomy. This pressure (or pressure change) may be provided as an input to the software module based on measured, predicted, a priori known, etc. values. The location of the craniotomy may also be provided as input.

Any of the previously described inputs, or any other input may be used in any combination to generate the output of the software module.

The output of the software module is the expected position of the soft tissues relative to the structural member of the patient's anatomy (to which a reference element is coupled). The output may include the position of the soft tissues, where this position is expressed as positions of various connected nodes. The output may be the position of a region of interest (e.g. the center of the region of interest). For a cranial surgical procedure, the output includes brain shift. The output may also be in the form of adjusted medical images of the brain accounting for movement due to the various inputs, including gravity.

FIG. 6 provides a flowchart of operations 600 which define a computer implemented method, such as for a computing unit 104, to perform a surgical procedure on soft tissues. At step 602, the operations compute a registration of a structural member of a patient's anatomy relative to a reference element coupled thereto. At step 604, the operations receiving inclinometer measurements from a sensor unit, the sensor unit comprising an optical sensor to generate optical measurements from a tracker and at least one sensor to provide inclination measurements, wherein the tracker is configured to provide positional information in up to six degrees of freedom to the optical sensor. At step 606, the operations calculating a direction of gravity relative to the structural member of the patient's anatomy based on the inclinometer measurements and the registration. At step 608, the operations determining spatial information of the soft tissues relative to the reference element based on the registration, the direction of gravity and expected soft tissue movement provided by a computer model modelling the mechanics of the soft tissues of the anatomy responsive to the direction of gravity. At step 610, the operations receive optical measurements from the sensor unit of the tracker attached to a surgical tool, and compute a position of the tool relative to the reference element based on the optical measurements. And, at step 612, the operations provide surgical navigation data for display, the surgical navigation data based on the position of the tool and the spatial information of the soft tissues.

The computer model of the anatomy may be based on any one or more of: a medical image of the anatomy; known material properties of tissues of the anatomy, including the soft tissues; a finite element model of the anatomy; a look-up table mapping expected soft tissue movement based on the direction of gravity; blood pressure; and pressure within the soft tissue cavity.

As noted previously, the reference element may be rigidly attached to the structural member. The reference element may be non-invasively attached to the structural member. The method steps to calculate, to determine, to receive optical measurements and to provide may be performed in real-time. The structural member of the patient's anatomy may be a skull, and the soft tissues may be the patient's brain. The reference element may be the sensor unit. The reference element may be the tracker. The registration may be performed using a registration tool with a tracker attached thereto.

The surgical navigation data may be relative to a surgical tool, where the surgical tool has a tracker attached thereto. Operations may further perform steps to receive medical image data; perform an image registration; and provide image guided surgical navigation for display.

Figure 7:
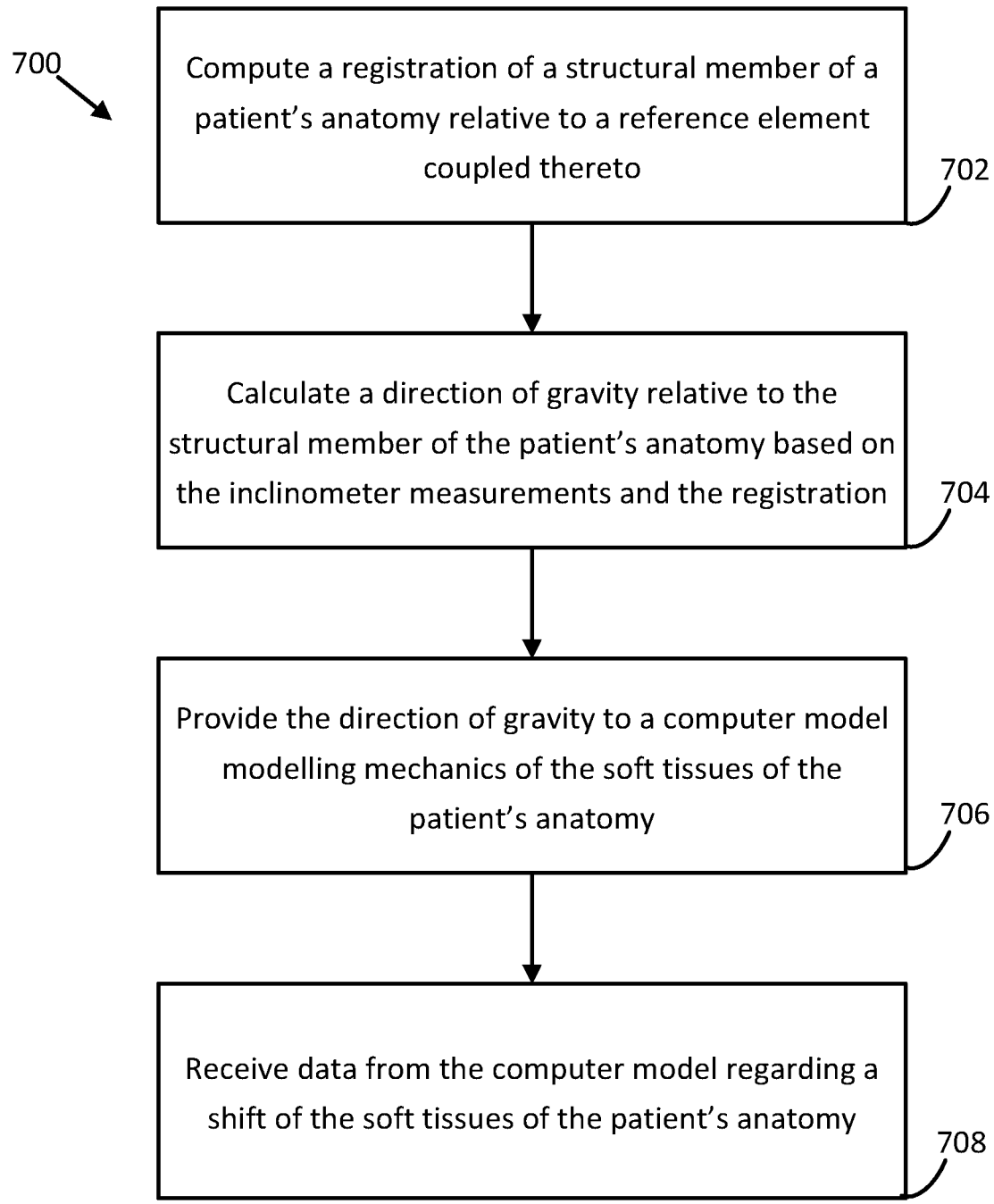

FIG. 7 is a flow chart of operations 700 to perform a surgical procedure on soft tissues of a patient's anatomy. At 702, operations compute a registration of a structural member of the patient's anatomy relative to the reference element. A sensor unit comprises an optical sensor to generate optical measurements from a tracker and at least one sensor to provide inclination measurements to determine a direction of gravity. The tracker is configured to provide positional information in up to six degrees of freedom to the optical sensor. The reference element is coupled the structural member.

At 704, operations calculate a direction of gravity relative to the structural member of the patient's anatomy based on inclination measurements and the registration. At 706, operations provide the direction of gravity to a computer model modelling the mechanics of the soft tissues of the anatomy; and, at 708, operations receive data from the computer model regarding a shift of the soft tissues of the anatomy.

The computer model may be provided by a remotely located computing unit (e.g. a server) relative to an intraoperative computing unit performing the steps of operations 700. The surgical procedure may be a cranial procedure and the shift may be a shift of a brain.

Operations 700 may provide surgical navigation data for display. The shift may be presented such as via a display unit. Operations 700 may receive optical measurements, from the sensor unit, of the tracker attached to a surgical tool, and compute a position of the tool relative to the reference element based on the optical measurements to provide as surgical navigation data. Operations 700 may further perform steps to receive medical image data; perform an image registration; and provide image guided surgical navigation for display.

In an exemplary system and/or in accordance with an exemplary computer implemented method, a computing unit does not provide a computer model of the soft tissue, but instead receives a vector representative of the direction of gravity during imaging (i.e. during the generation of a medical image). The computing unit, based on a registration and/or image registration, may use inclination measurements of a reference element, and the vector representative of the direction of gravity during imaging to calculate the patient's current orientation with respect to the patient's orientation during imaging, and provide this information to a display unit for communication to a user in real-time. The user may act on this information to bring the patient's anatomy into alignment with how they were oriented (i.e. a similar or substantially similar orientation) during imaging. This may minimize the influence of gravity when performing surgical procedures with reference to the medical image particularly in surgeries where accuracy requirements are high. The orientation of the patient during the procedure with respect to the orientation during imaging may be communicated by any means, including numerically, graphically (e.g. bubble level graphic), or otherwise. This information may be displayed prior to or during surgical navigation, and may be displayed in real-time, such that any movement of the patient during the surgery may be detected and the surgeon may re-adjust the position of the patient based on the detected movement. Alternatively, the computing unit may cease to display surgical navigation if a difference in the orientation of the patient during the procedure and the orientation of the patient during imaging exceeds a pre-set threshold.

Figure 8:
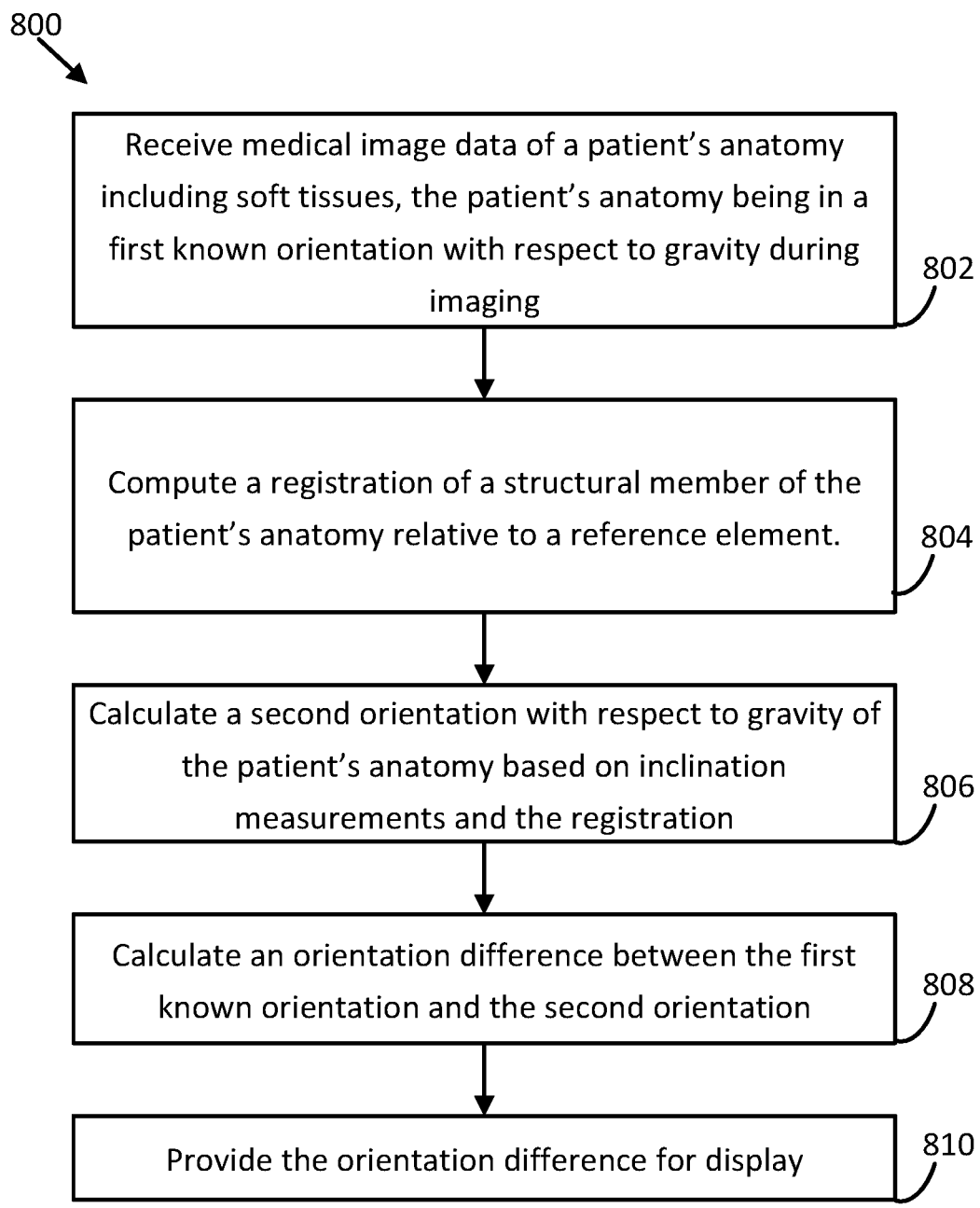

FIG. 8 is a flowchart of operations 800 which define a computer implemented method, such as for a computing unit 104, to perform a surgical procedure on soft tissues. At 802, operations receive medical image data of a patient's anatomy including soft tissues, the patient's anatomy being in a first known orientation with respect to gravity during imaging.

At 804, operations compute a registration of a structural member of the patient's anatomy relative to a reference element. A sensor unit, comprising an optical sensor generates optical measurements from a tracker. The sensor unit also comprises at least one sensor to provide inclination measurements to determine a direction of gravity. The tracker is configured to provide positional information in up to six degrees of freedom to the optical sensor. A reference element is coupled with a structural member of a patient's anatomy.

At 806, operations calculate a second orientation with respect to gravity of a patient's anatomy based on inclination measurements and the registration. At 808, operations calculate the orientation difference between the first known orientation and the second orientation. And, at 810, operations provide the orientation difference for display.

Operations may be configured such that the orientation difference is provided as a bubble level graphic. Operations may provide surgical navigation of a surgical tool with respect to soft tissues. The surgical tool may be coupled to a tracker and the sensor unit provide optical measurements such that the operations determine the pose of the surgical tool, in real time, during the procedure. Operations may persistently display the orientation difference during surgical navigation. Operations may not display the surgical navigation when the orientation difference exceeds a threshold. The orientation difference may be calculated and displayed in real time during surgical navigation.

In another exemplary system and/or in accordance with another exemplary computer implemented method, a computing unit does not provide a computer model of the soft tissue, nor does the computing unit receive a vector representative of the direction of gravity during imaging. The computing unit executes instructions providing to a display unit the current direction of gravity with respect to the patient (e.g. shown as a vector overlaid on an image-guided display, such as the one depicted in FIG. 3). This display provides the surgeon with knowledge about the direction of gravity relative to the patient's anatomy during surgery. This knowledge may allow the surgeon to adjust a surgical plan (for example, based on the direction of gravity, the surgeon may decide to perform a more aggressive excision of a tumour around its margin facing the direction of gravity, in anticipation that the tumour has shifted slightly in that direction).

In the systems and methods described herein, measurements of the direction of gravity with respect to the reference element are used in real-time for surgical navigation. In this way, if a patient's rigid anatomical structure or structural member (e.g. skull) moves during the procedure (unintentionally, or due to repositioning), the current real-time direction of gravity is used. The computing unit shown and described here may take different forms. The computing unit may comprise a single computing device (e.g. laptop, workstation, tablet, etc., or multiple computing devices (a computing device with a server, etc.). Medical image data may be accessed by various technologies including a network connection to imaging database, a USB key, a direct connection to imaging equipment, etc.

The computing device may receive input from one or more user input devices including but not limited to a keyboard, a mouse or other pointing device, a touch screen or other gestural interface, a microphone for audio (voice) commands, etc.

A person skilled in the art will realize that the specification is applicable to other forms of surgery and is not meant to be limited to brain surgery. It is further understood that various methods described for performance by a computer system such as navigational surgery may be implemented in software such as instructions and data to configure at least one processing unit of a computer system to perform the method. The instructions and data may be stored in a device such as a memory (RAM, ROM, flash drive, etc.) or other non-transitory storage device (e.g.: magnetic, optical, or other disk or storage medium).

Accordingly, it is to be understood that this subject matter is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible.

The invention claimed is:

1. A system to perform a surgical procedure on soft tissues comprising:
   a tracker;
   a sensor unit, comprising an optical sensor to generate optical measurements from the tracker and at least one other sensor to provide inclination measurements to determine a direction of gravity,
      wherein the tracker is configured to provide positional information in up to six degrees of freedom to the optical sensor,
      wherein one of the sensor unit or the tracker is adapted to couple with a structural member of a patient's anatomy, and
      wherein the soft tissues have a nominal position relative to the structural member of the patient's anatomy; and
   a computing unit configured to:
      compute a registration of the structural member of the patient's anatomy relative to the one of the sensor unit or the tracker coupled with the structural member;
      calculate the direction of gravity relative to the structural member of the patient's anatomy based on the inclination measurements and the registration;
      determine spatial information of the soft tissues relative to the one of the sensor unit or the tracker coupled with the structural member based on the registration, the direction of gravity relative to the structural member, and expected soft tissue movement provided by a computer model modelling mechanics of the soft tissues responsive to the direction of gravity relative to the structural member,
         wherein the spatial information of the soft tissues is an expected position of the soft tissue relative to the structural member of the patient's anatomy; and
      provide surgical navigation data for display.

2. The system of claim 1, wherein the one of the sensor unit or the tracker adapted to couple with the structural member is adapted to rigidly attach to the structural member.

3. The system of claim 1, wherein the one of the sensor unit or the tracker adapted to couple with the structural member is adapted to non-invasively attach to the structural member.

4. The system of claim 1, wherein the computing unit, in real-time, calculates the direction of gravity relative to the structural member of the patient's anatomy, determines the spatial information of the soft tissues, and provides the surgical navigation data.

5. The system of claim 1, wherein the structural member of the patient's anatomy is a skull, and wherein the soft tissues are a brain of the patient's anatomy.

6. The system of claim 1, wherein the sensor unit is adapted to couple with the structural member of the patient's anatomy.

7. The system of claim 1, wherein the tracker is adapted to couple with the structural member of the patient's anatomy.

8. The system of claim 1, wherein the registration is performed using a registration tool with the tracker or another tracker attached to the registration tool.

9. The system of claim 1, wherein the surgical navigation data is relative to a surgical tool, wherein the surgical tool has the tracker or another tracker attached to the surgical tool.

10. The system of claim 1, wherein the computing unit is further configured to:
    receive medical image data;
    perform an image registration; and
    provide image guided surgical navigation data for display.

11. The system of claim 1, wherein the expected position of the soft tissue is expressed as positions of connected nodes.

12. The system of claim 1, wherein the expected position of the soft tissue is expressed as a position of a region of interest of the soft tissue.

13. The system of claim 1, wherein the expected position of the soft tissue is expressed as adjusted medical images accounting for movement of the soft tissue due to the gravity.

14. The system of claim 1, wherein the soft tissue is located within the structural member.

15. The system of claim 14, wherein the soft tissue comprises a brain and the structural member comprises a skull.

16. A computer implemented method to perform a surgical procedure on soft tissues comprising steps of:
    computing a registration of a structural member of a patient's anatomy relative to a sensor unit coupled to the structural member,
       wherein the soft tissues have a nominal position relative to the structural member;
    receiving inclination measurements from the sensor unit, the sensor unit comprising an optical sensor to generate optical measurements from a tracker and at least one sensor to provide inclination measurements,
       where in the tracker is attached to a surgical tool, and
       wherein the tracker is configured to provide positional information in up to six degrees of freedom to the optical sensor;
    calculating a direction of gravity relative to the structural member of the patient's anatomy based on the inclination measurements and the registration;
    determining spatial information of the soft tissues relative to the sensor unit based on the registration, the direction of gravity relative to the structural member, and expected soft tissue movement provided by a computer model of the patient's anatomy modelling mechanics of the soft tissues responsive to the direction of gravity relative to the structural member,
wherein the spatial information of the soft tissues is an expected position of the soft tissue relative to the structural member of the patient's anatomy;

receiving, from the optical sensor of the sensor unit, the optical measurements from the tracker;

computing a position of the surgical tool relative to the sensor unit based on the optical measurements; and providing surgical navigation data for display, the surgical navigation data based on the position of the surgical tool and the spatial information of the soft tissues.

17. The method of claim 16, wherein the computer model of the patient's anatomy is based on any one or more of: a medical image of the patient's anatomy; known material properties of tissues of the patient's anatomy, including the soft tissues; a finite element model of the patient's anatomy; a look-up table mapping the expected soft tissue movement based on the direction of gravity relative to the structural member; blood pressure; and pressure within a cavity containing the soft tissue.

18. The method of claim 16, wherein the sensor unit is rigidly attached to the structural member.

19. The method of claim 16, wherein the sensor unit is non-invasively attached to the structural member.

20. The method of claim 16, wherein the method calculates, in real time, the direction of gravity relative to the structural member of the patient's anatomy, determines the spatial information of the soft tissues, and provides the surgical navigation data.

21. The method of claim 16, wherein the structural member of the patient's anatomy is a skull, and wherein the soft tissues are a brain of the patient's anatomy.

22. The method of claim 16, wherein the soft tissue is located within the structural member.

23. The method of claim 22, wherein the soft tissue comprises a brain and the structural member comprises a skull.

* * * * *